United States Patent [19]

Klieman et al.

[11] 4,452,376
[45] Jun. 5, 1984

[54] HEMOSTATIC CLIP APPLICATOR

[75] Inventors: Charles H. Klieman, 3737 Century Blvd., Lynwood, Calif. 90262; Richard M. Densmore, South Gate, Calif.

[73] Assignee: Charles H. Klieman, Los Angeles, Calif.

[21] Appl. No.: 471,322

[22] Filed: Mar. 2, 1983

Related U.S. Application Data

[60] Continuation of Ser. No. 175,482, Aug. 5, 1980, abandoned, which is a division of Ser. No. 822,076, Aug. 5, 1977, abandoned.

[51] Int. Cl.³ .................. B65H 1/14; B65H 3/24; A61B 17/12
[52] U.S. Cl. .................. 221/198; 128/325; 128/334 R; 221/243; 227/DIG. 1
[58] Field of Search .......... 221/191, 198, 232, 260, 221/279, 280; 128/325, 334 R; 227/DIG. 1

[56] References Cited

U.S. PATENT DOCUMENTS

| | | | |
|---|---|---|---|
| 2,277,139 | 3/1942 | Niemand | 128/337 UX |
| 2,874,384 | 2/1959 | Krone | 227/19 |
| 3,032,039 | 5/1962 | Beaty | 227/19 |
| 3,082,426 | 3/1963 | Miles | 128/334 R |
| 3,231,976 | 2/1966 | Wallshein | 227/19 UX |
| 3,234,636 | 2/1966 | Brown | 128/334 R |
| 3,598,281 | 8/1971 | Watermeier | 221/198 |
| 3,601,302 | 8/1971 | Potekhina et al. | 227/19 |
| 3,780,416 | 12/1973 | Rider | 227/DIG. 1 X |
| 4,108,306 | 8/1978 | Samuels et al. | 221/279 X |
| 4,166,466 | 9/1979 | Jarvik | 128/325 |
| 4,201,314 | 5/1980 | Samuels et al. | 221/198 |
| 4,296,751 | 10/1981 | Blake et al. | 128/325 |

FOREIGN PATENT DOCUMENTS 2088723 6/1982 United Kingdom .

Primary Examiner—Robert B. Reeves
Assistant Examiner—Edward M. Wacyra
Attorney, Agent, or Firm—Spensley, Horn, Jubas & Lubitz

[57] ABSTRACT

A magazine for a hemostatic clip applicator useful in the rapid and automatic application of hemostatic clips for the strangulation of tubular members. The magazine has a housing wherein a plurality of clips are stored. A clip loading mechanism disposed within the housing urges the clips through the housing to a clip feed mechanism. The clip feed mechanism sequentially moves the clips to a clip deforming mechanism of the clip applicator.

32 Claims, 22 Drawing Figures

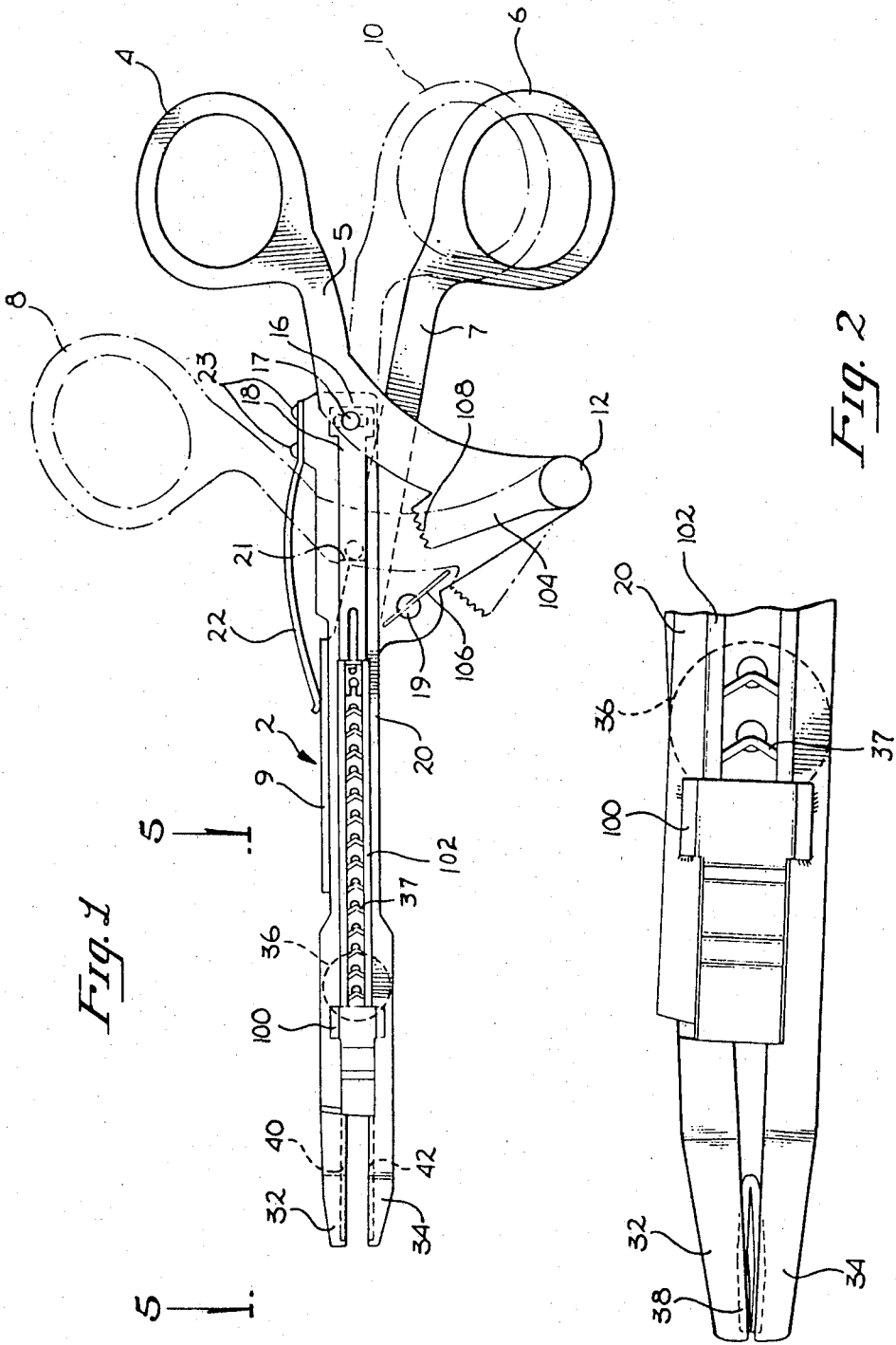

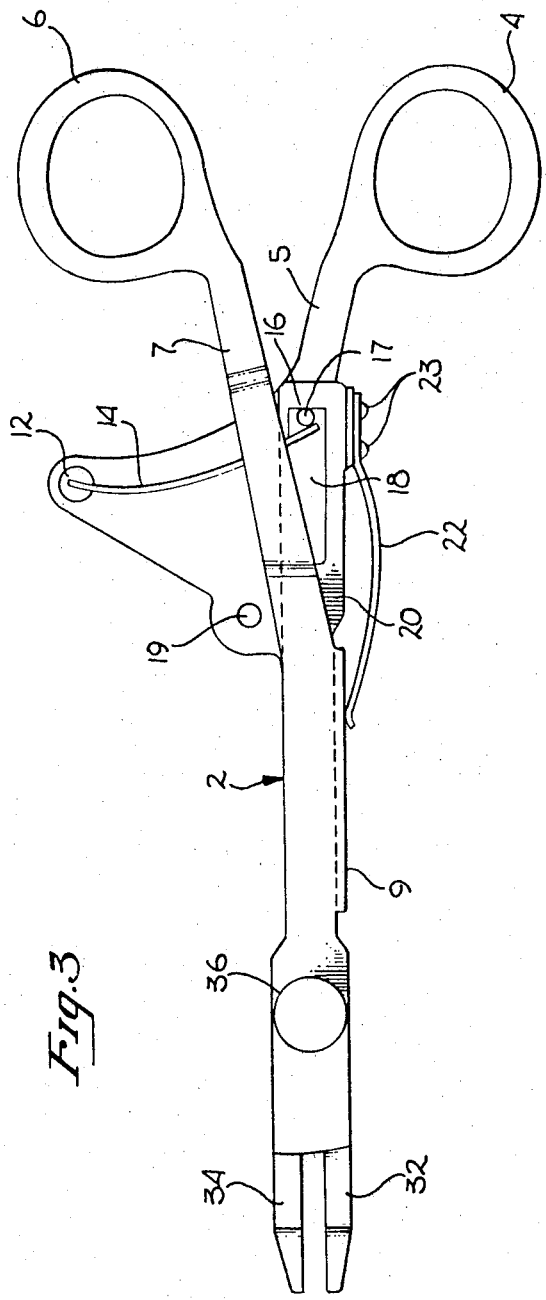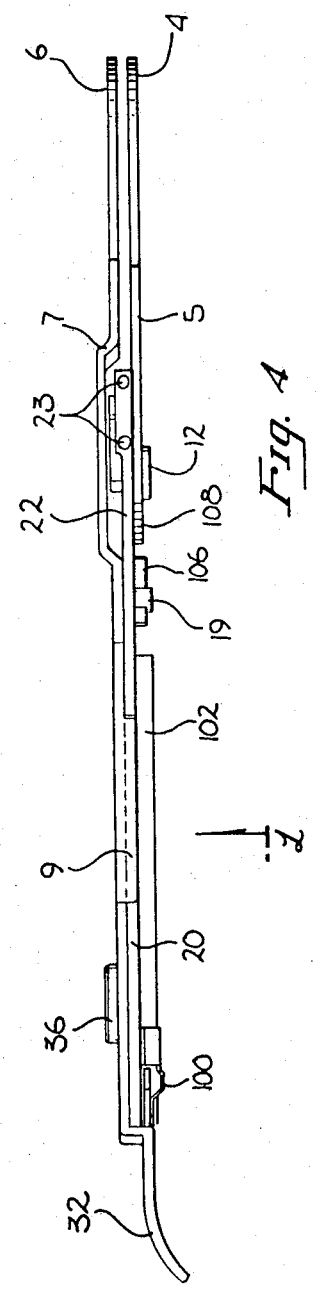
Fig. 3
Fig. 4

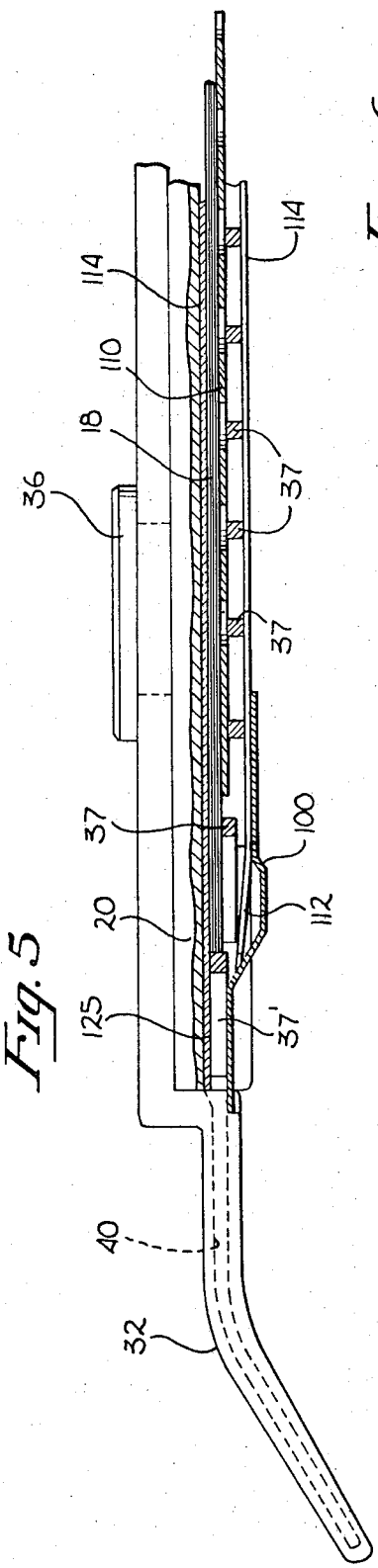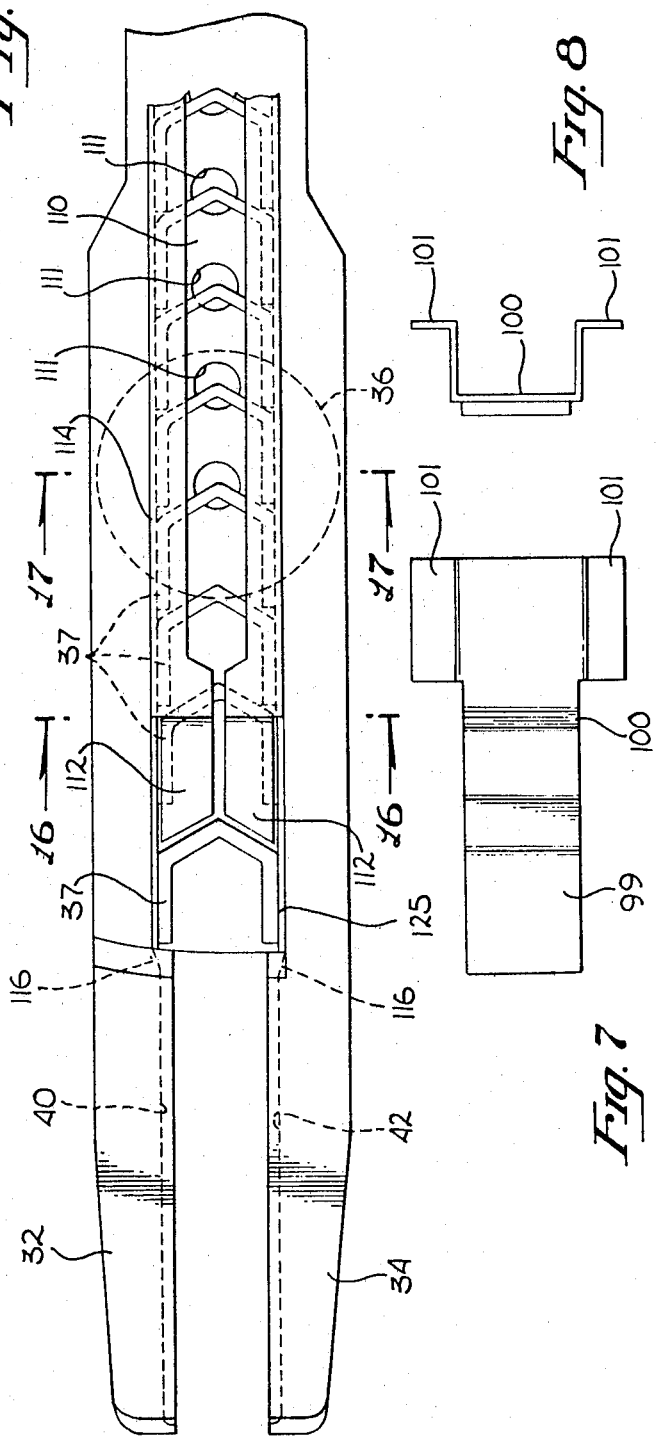

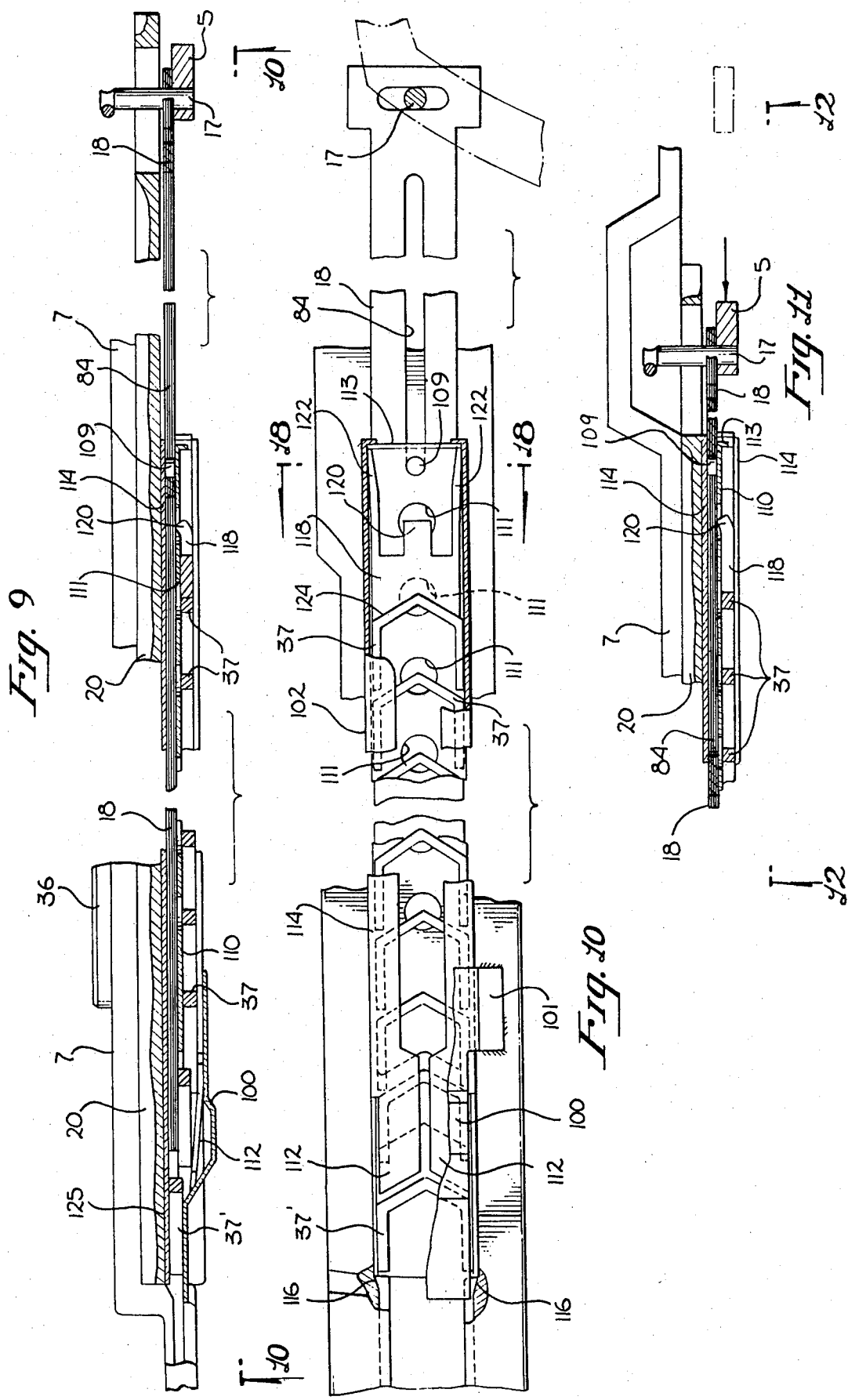

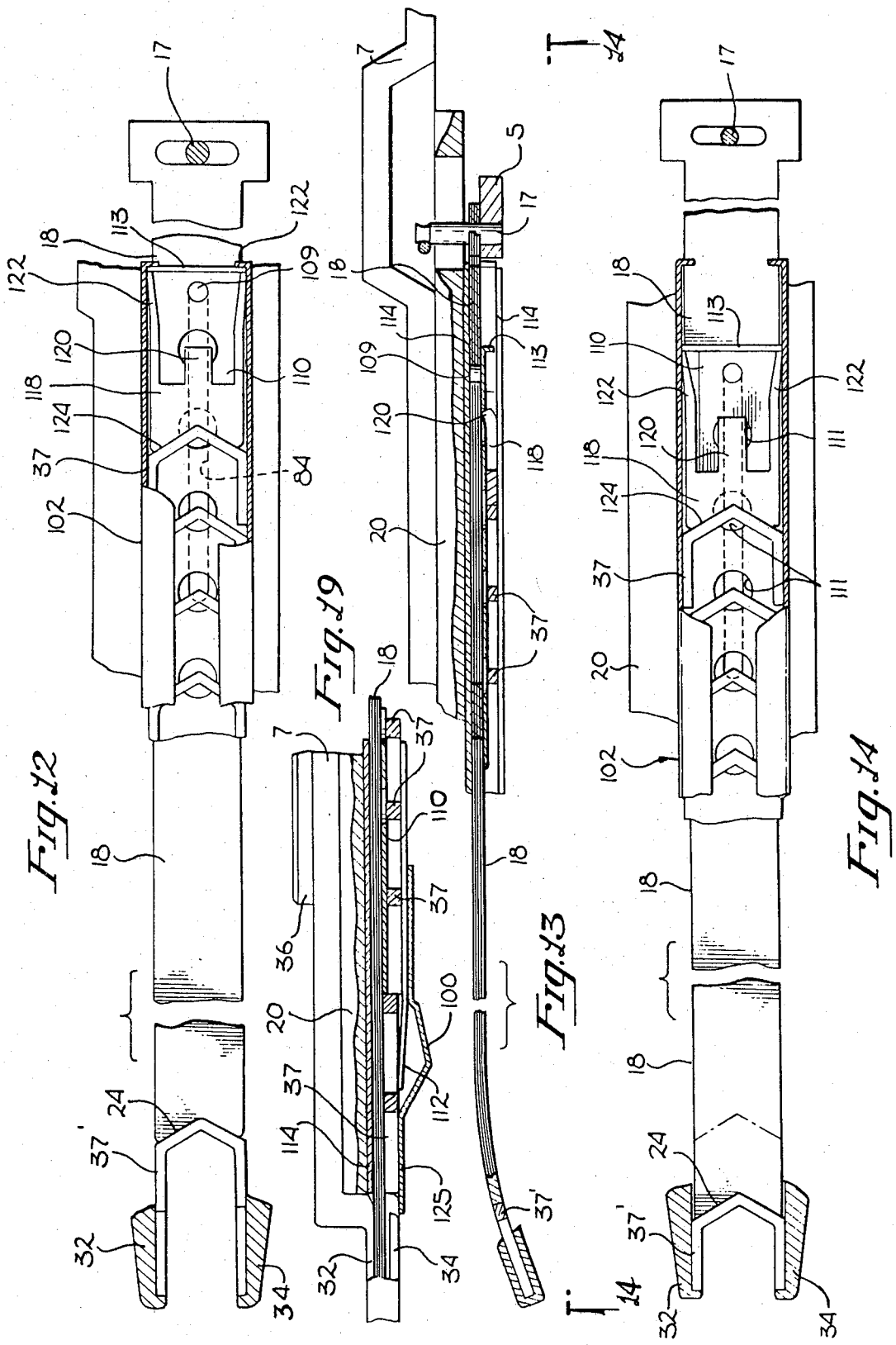

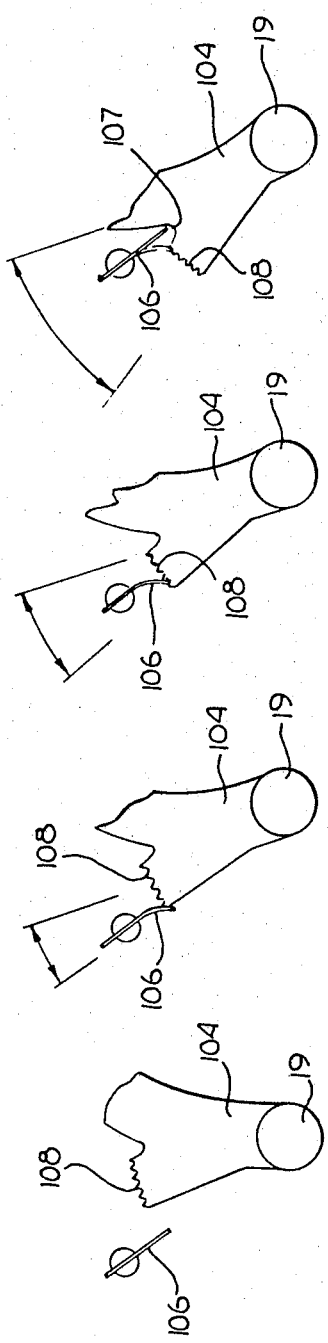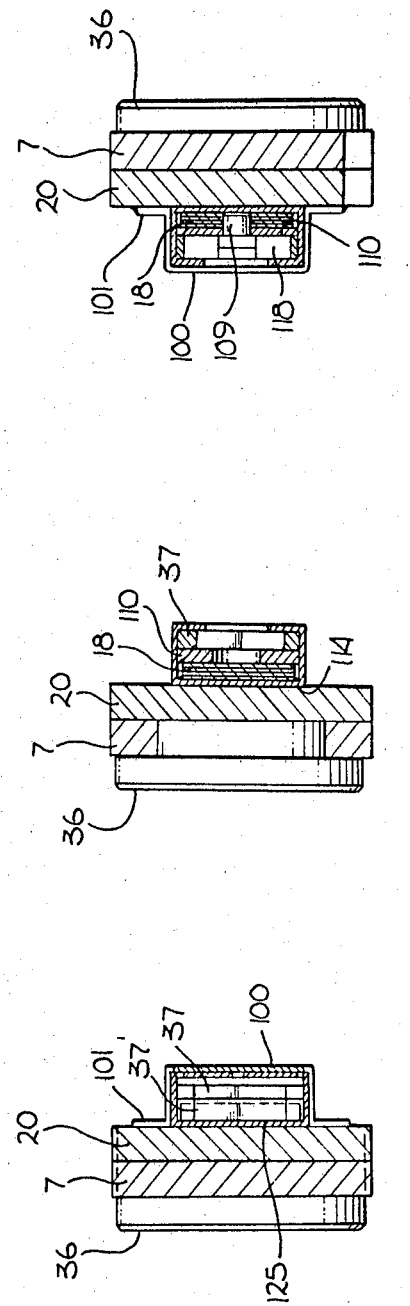

HEMOSTATIC CLIP APPLICATOR

This is a continuation of Ser. No. 175,482 filed on Aug. 5, 1980, now abandoned; which is a division of Ser. No. 822,076 filed on Aug. 5, 1977, now abandoned.

BACKGROUND OF THE INVENTION

1. Copending Patent Applications

In copending U.S. Patent Application Ser. No. 822,096 entitled SURGICAL STAPLER filed Aug. 5, 1977, now abandoned, and assigned to the present assignee, a hemostatic clip applicator for the strangulation of tubular members in a rapid and automatic manner is disclosed. Also, in copending U.S. Patent Application Ser. No. 822,095, now U.S. Pat. No. 4,188,953, entitled HEMOSTATIC CLIP filed Aug. 5, 1977, and assigned to the present assignee, hemostatic clips adapted for utilization in the present invention and similar devices is disclosed. The former copending patent application entitled SURGICAL STAPLER is directed, in part, to a device having a main body and a disposable clip cartridge which may be attached and removed from the main body. Disposed within the clip cartridge are a plurality of hemostatic clips, while disposed within the main body is a clip feed means which moves clips, which have been fed into the main body, to clip deforming jaws where the clips are deformed about a blood vessel or the like.

While the applicator noted in the preceding paragraph provides a novel method for automatically closing blood vessels and other fluid ducts, refinements can be made so that the entire device, including the main body, can be made more inexpensively. Such an inexpensive device may then be sterilized by the manufacturer, packaged to maintain the sterilization, and then entirely disposed of following a single use. In particular, the device of the copending application required careful machining of a slot through the main body so that the feed means would be accurately guided therethrough. Furthermore, that device required the use of a separate lost motion link to provide the necessary sequential actuation. It is toward the refinement of the device disclosed in the copending U.S. patent application noted above that the present invention is directed, and more specifically, toward a device which can be inexpensively stamped instead of machined and which requires fewer parts.

2. Field of the Invention

The invention relates to the field of devices useful in the application of hemostatic clips, and more specifically, to devices for the application of hemostatic clips used in the strangulation of blood vessels and other fluid ducts.

3. Prior Art

In a typical surgery procedure, a great many veins, arteries, and other blood vessels must be severed and closed. This is often a difficult and time consuming procedure since many vessels are located in obscure areas where there is little room in which to work. Thus, it is apparent that a device which would reduce the time required for closure of blood vessels would be of great benefit to both the surgeon and the patient. However, in the modern surgery environment, such a device should be simply and effectively constructed so that its cost will allow for disposal of the device following usage by the surgeon, thereby eliminating the necessity of costly re-sterilization.

One prior art attempt to provide a device which can more rapidly close a blood vessel is disclosed by Wood, U.S. Pat. No. 3,326,216. The Wood device consists of a hemostat-like instrument which has finger loop portions coupled to jaw portions. The jaw portions are adapted to hold a hemostatic clip therebetween so that the clip may be closed about a vessel by bringing the finger loops together. Wood also discloses a separate cartridge which holds a plurality of clips. When the Wood device is to be used, the jaw portions are placed about one clip contained in the cartridge, and the clip is removed from the cartridge by the engagement of the clip by the jaw portions. When the clip has been used, a new clip may be placed in the device by returning to the clip cartridge and inserting a new clip. Two problems are apparent with the Wood device. First, the hemostatic clips are not automatically fed into the jaws of the device, but must be individually placed there. This procedure is time consuming and cumbersome. In addition, the Wood device is capable of expanding its jaws wider than the width of a clip contained therein. Thus, a clip may be accidentally droped from the device causing a great deal of inconvenience and delay.

A second prior art attempt to provide more rapid yet effective strangulation of blood vessels and the like is described by Miles, U.S. Pat. No. 3,082,426. Miles discloses a surgical stapling device which consists of finger loops coupled to a pair of arms which terminate in jaw portions, the jaw portions being adapted to grasp and hold a tubular member. The device also has a magazine for holding a plurality of clips along the length of one arm, and manually operable clip ejector means for placing a clip about the tubular member which is to be closed. In operation, the tubular member is first grasped and held by the jaw portions of the Miles device. The surgeon then places his index finger on a button attached to the clip ejector. By urging the button forward, the clip ejector places a clip about the tubular member. Then, the clip may be deformed about the blood vessel by bringing the pair of finger loops together. An obvious disadvantage of the Miles device is that it is cumbersome, in that the surgeon must manually move a clip between the jaws of the device while holding the device steady so as not to loose the grasp of the tubular member. Also, as the clips are used from the cartridge, the button moves farther foward so that it becomes more and more difficult to reach. Furthermore, this procedure is time consuming in that each individual clip must be manually fed between the jaws of the stapling device. Finally, the construction of the Miles device, particularly in the jaw portions, provides poor visability to the surgeon since the thickness of the device obscures the vessels which are to be closed.

Another prior art attempt to provide rapid application of hemostatic clips is disclosed by DeCarlo, U.S. Pat. No. 3,740,944. DeCarlo discloses a gun-like device for suturing and severing blood vessels in a three stage procedure. First, jaws of the device are closed about the blood vessel by the actuation of the gun-like trigger mechanism. Second, a pair of pushers extend through the device and come forward to crimp a pair of clips, brought from an internal magazine, about the vessel in two spaced locations. Third, a blade comes forward from the device upon further actuation of the gun-like handles and severs the blood vessel between the two clip locations.

The internal clip magazine of the DeCarlo device uses a pair of leaf spring assemblies to index a plurality of pairs of hemostatic clips. The clips are stored in a pair of index guide rails where they are moved forward in unison by opposing leaf spring assemblies. One leaf spring assembly is attached to the moveable main body portion while the opposing leaf spring assembly is affixed to one guide rail. When the gun-like handles are actuated, the leaf spring assembly attached to the main body moves forward and contacts portions of the clips contained within the magazine. Further movement of the main body portion moves individual clips along the index guide rail and ultimately ejects a pair of clips. When a pair of clips has been ejected, the main body portion begins to return to its original static position. During this rearward movement of the main body portion, there is a transference of a pair of clips from the index guide rails to the ejection guide rails. This transference occurs when each leaf spring assembly and its corresponding ramp portions guide a clip from one index guide rail to the ejection guide rail where it is available for loading into the front portion of the instrument.

One problem with the DeCarlo device is that, due to the three stage operation, the device is necessarily bulky. This is a major disadvantage in that many surgical procedures require severence and closure of blood vessels in very limited areas so that a bulky instrument may not be able to reach the required vessel. The bulkiness of the device also creates a further disadvantage in that it produces a lack of visibility for the surgeon. Thus, the very vessel that is to be severed and closed may be obscured since the surgeon may not be able to see around the device. A further disadvantage stems from the fact that the DeCarlo device does not adapt to the application of a single clip, but only applies a pair of clips to the vessel to be closed. In a great many surgical procedures, only the application of one clip is desired while the application of two clips would only complicate the severance procedure.

Accordingly, it is a general object of the present invention to provide an improved hemostatic clip applicator device for the strangulation of blood vessels and the like.

It is another object of the present invention to provide an improved hemostatic clip applicator device which automatically feeds clips to its forward portion and then provides automatic deformation of the clips about blood vessels.

It is yet another object of the present invention to provide an improved hemostatic clip applicator device which provides high visibility to the user.

It is yet another object of the present invention to provide an improved hemostatic clip applicator device which is simply constructed and relatively inexpensive so that the entire device is disposable after a single use.

It is a still further object of the present invention to provide an improved hemostatic clip applicator device which is incapable of accidentally dropping clips from the device.

SUMMARY OF THE INVENTION

A hemostatic clip applicator device useful for rapidly and automatically applying clips for the strangulation of blood vessels and the like is provided. The device has a clip magazine means coupled to the exterior of a main body, the clip magazine means being adapted to hold a plurality of hemostatic clips. Attached to one end of the main body is a clip deforming means adapted to hold and crimp a hemostatic clip about a blood vessel. Slideably disposed within the clip magazine means is a clip feed means which is adapted to move clips from the magazine means to the clip deforming means. Coupled to the clip feed means and the clip deforming means are actuating means. By a sequential forward and rearward movement of the actuating means, a hemostatic clip is moved from the clip magazine means to the clip deforming means and there crimped about a blood vessel or the like. This sequence of feeding clips to the clip deforming means and crimping them therein, may be repeated until the plurality of clips located in the clip magazine means is depleted. The applicator device is simply yet effectively designed so that it can be manufactured and sold at a relatively low cost. Such low cost allows the device to be used once and then disposed of.

The novel features which are believed to be characteristic of the invention, both as to its organization and its method of operation, together with further objects and advantages thereof, will be better understood from the following description in connection with accompanying drawings in which a presently preferred embodiment of the invention is illustrated by way of example. It is to be expressly understood, however, that the drawings are for the purposes of illustration and description only and are not intended as a definition of the limits of the invention.

BRIEF DESCRIPTION OF THE DRAWINGS

FIG. 1 is a side view of the clip applicating device of the present invention;

FIG. 2 is an enlarged view of the jaw portions of the present invention showing a hemostatic clip closed by the clip applicating device;

FIG. 3 is a side view of the back side of the clip applicating device of the present invention;

FIG. 4 is a top view of the clip applicating device of the present invention, showing the curved jaw portions;

FIG. 5 is an enlarged view of the top forward portion of the clip applicating device of the present invention;

FIG. 6 is an enlarged view of the side of the forward portion of the clip applicating device;

FIG. 7 is an enlarged view of the guide spring means of the present invention;

FIG. 8 is an end view of the guide spring means of the present invention;

FIG. 9 is a top cut-away view of a portion of the clip applicating device of the present invention;

FIG. 10 is a side cut-away view of the clip magazine means of the present invention;

FIG. 11 is a top cut-away view of the clip magazine of the present invention;

FIG. 12 is a side cut-away view of the clip magazine of the present invention;

FIG. 13 is a top cut-away view of the clip applicating device of the present invention;

FIG. 14 is a side cut-away view of a portion of the clip applicating device of the present invention;

FIGS. 15a, 15b, 15c and 15d are a series of views illustrating the operation of the safety ratchet of the present invention;

FIG. 16 is a cross-sectional view of the applicating device of the present invention taken along line 16—16 of FIG. 6 of the present invention;

FIG. 17 is a cross-sectional view of the applicating device of the present invention taken along line 17—17 of FIG. 6;

FIG. 18 is a cross-sectional view of the applicating device of the present invention taken along line 18—18 of FIG. 10; and FIG. 19 is a top cut-away view of a portion of the clip applicating device of the present invention.

DETAILED DESCRIPTION OF THE INVENTION

A hemostatic clip applicator device is disclosed which is useful in rapidly applying a hemostatic clip about blood vessels and other fluid ducts. The hemostatic clip applicator of the present invention may be used with hemostatic clips such as is described in our co-pending application, Ser. No. 822,095, now U.S. Pat. No. 4,188,953, filed on Aug. 5, 1977 entitled HEMOSTATIC CLIP, or with any other suitably adapted hemostatic clip.

Referring to FIG. 1, the hemostatic clip applying device 2 of the present invention is shown in its static configuration. Clip applying device 2 has an actuating means comprised of an upper handle portion and a lower handle portion. In the presently preferred embodiment, the upper handle portion is comprised of upper finger loop 4, and upper finger loop member 5, while the lower handle portion is comprised of lower finger loop 6 and lower finger loop member 7. It can be seen in phantom in FIG. 1 that upper finger loop 4 may be brought to its forward position 8, while lower finger loop 6 may be moved to an inward position 10. Upper finger loop 4 and upper finger loop member 5 pivot about upper finger loop pivot 12. Upper finger loop member 5 is coupled to clip feed blade 18 by feed blade pivot 17.

As will be more fully described hereinbelow, clip feed blade 18 is a clip feed means which in the presently preferred embodiment is a blade member adapted to slide through clip magazine means 102 and into the forward portions of device 2 by the forward movement of upper finger loop 4. Upper finger loop 4 will continue to move clip feed blade 18 through clip magazine 102 until feed blade pivot 17 abuts stop means 21. Disposed within clip magazine means 102 are a plurality of hemostatic clips 37, and magazine 102 is adapted such that the individual clips are available to be moved forward by clip feed blade 18. Spring guide means 100 aids the movement of a clip from magazine 102.

Coupled to the forward portion of main body 20 is a clip deforming means adapted to deform a hemostatic clip about a blood vessel or the like. In the presently preferred embodiment, the clip deforming means is comprised of upper jaw portion 32 and lower jaw portion 34. Upper jaw portion 32 is fixedly coupled to lower finger loop member 7 and pivotally coupled to main body 20 by upper jaw pivot 36, while lower jaw portion 34 is fixedly coupled to main body 20. When a hemostatic clip has been fed from the clip magazine 102 into grooves 40 and 42 of jaw portions 32 and 34 by clip feed blade 18, the clip may be squeezed about a blood vessel by first returning upper finger loop 4 to its rearward position and then raising finger loop 6 to its phantom position 10 so that upper jaw portion 32 closes toward lower jaw portion 34.

It is important to note that the outward movement of upper jaw portion 32 is limited by the abutment of main body 20 with lower finger loop member tab portion 9 which extends over main body 20. Thus, if a hemostatic clip is located in jaw portions 32 and 34, it may not be accidentally dropped by the over expansion of upper jaw 32. Lower finger loop 6 and lower finger loop member 7 are biased toward their static configuration by second spring means 22, which is coupled to main body 20 by rivets 23, so that upper jaw portion 32 will return to its open position when lower finger loop 6 is no longer raised to its phantom position 10. Also shown in FIG. 1 is a safety rachet 104, rachet spring 106 and ratchet teeth 108. As will be described more fully hereinbelow, safety ratchet 104 in combination with spring 106 and teeth 108 ensures that a clip is fed fully into jaw portions 32 and 34. Of course, clip applying device 2 is fully functional, in an alternate embodiment, without safety ratchet 104, spring 106 and teeth 108.

FIG. 2 illustrates the jaw portions 32 and 34 as they are closed about a deformed clip 38. This configuration would have resulted from the feeding of a clip into the jaw portions 32 and 34 by the forward movement of upper finger loop 4, followed by the rearward movement of upper finger loop 4 and then the inward movement of lower finger loop 6. It may be noted that rearward movement of upper finger loop 4 has caused feed blade 18 to return to its unactuated position, thus exiting jaw portions 32 and 34, so that the jaw portions are free to close about a clip. FIG. 2 also illustrates guide spring means 100 as it is coupled to main body 20 and overlapping magazine 102.

FIG. 3 is a view of the reverse side of clip applying device 2. Shown in this view is the relationship of lower finger loop 6 and lower finger loop member 7 with main body 20 and upper jaw portion 32. Lower finger loop member 7 is fixedly secured to upper jaw portion 32 while the combination of member 7 and jaw portion 32 are pivotally coupled to main body 20 by upper jaw pivot 36. It can be seen that maximum outward travel of lower finger loop 6, and thus the maximum expansion of upper jaw portion 32, is limited by the abutment of lower finger loop tab portion 9 with main body 20. Also shown in FIG. 3 is first spring means 14 which is coupled to main body 20 at upper finger loop pivot 12 and which is configured to urge feed blade pivot 17, and thus clip feed blade 18, rearward. Second spring means 22 is coupled to main body 20 by rivets 23 and adapted to urge lower finger loop 6 outward to its static position.

FIG. 4 is a top view of clip applying device 2. Illustrated here is the relationship between main body 20, lower finger loop member 7 and upper jaw portion 32. It can be seen that lower finger loop member 7 is fixedly coupled to upper jaw portion 32 and lower finger loop 6, while the combination of member 7 and jaw portion 32 is pivotally coupled to main body 20 by upper jaw pivot 36. Thus, rotation of member 7 about pivot 36 by movement of lower finger loop 6 results in rotation of upper jaw 32 about pivot 36. Therefore, inward and outward movement of lower finger loop 6 will result in movement of upper jaw portion 32 toward and away from lower jaw portion 34. Also shown in FIG. 4 is the curved configuration of upper jaw portion 32 and lower jaw portion 34. This curved forward portion of clip applying device 2 provides the distinct advantage of improved visability during usage since the vessel which is to be closed will be located to one side or the other of the main body 20. Although the presently preferred embodiment of the upper and lower jaw portions utilizes a curved configuration, other configurations, such as straight jaw portions, may be used. Further illustrated in FIG. 4 are top views of clip magazine 102, guide spring means 100, second spring means 22 with its rivets 23, along with ratchet spring 106 and ratchet teeth 108.

FIG. 5 is a cross-sectional top view of the forward portion of clip applying device 2. Clip magazine 102, comprised of magazine housing 114, is coupled to the main body 20 of clip applying device 2. Longitudinally disposed within clip magazine 102 is clip feed blade 18, and ratchet blade 110. Also disposed within clip magazine 102 are a plurality of hemostatic clips 37. It can be seen from FIG. 5 that the forward movement of clip feed blade 18 through magazine 102 will move hemostatic clip 37' from its key position 125 through upper jaw portion groove 40 and ultimately to the extreme end of upper jaw 32. As noted in FIG. 4, jaw portions 32 and 34 are curved away from main body 20. Thus, feed blade 18 must be configured so as to be capable of being moved forward through grooves 40 and 42 while simultaneously bending away from main body 20 in grooves 40 and 42. In the presently preferred embodiment, this capability has been provided by constructing feed blade 18 of four layers of thin blades of metal in a laminated configuration. The four layers are only coupled at discrete points so that feed blade 18 is able to move longitudinally through main body 20 while curving around grooves 40 and 42 in jaw portions 32 and 34. Guide spring means 100 is adapted to maintain clip 37' in its key position 125 until clip 37' is moved forward by feed blade 18. In addition, leaf spring 112 is adapted to maintain the clip adjacent clip 37' in its proper position so that ultimately ratchet blade 110 will move clip 37 so as to replace clip 37'. It can also be seen in FIG. 5 that clip magazine 102 is comprised of a simply constructed housing 114 which, in the presently preferred embodiment, is spot-welded to main body 20. This method of forming and attaching the magazine 102 allows housing 114 to be inexpensively stamped from stock material and then attached to the main body 20. In contrast to the machining of a similarly configured groove through main body 20, this method of attaching a pre-formed magazine housing is considerably less expensive. Of course, clip magazine 102 may be coupled to the main body 20 of clip applying device 2 by a variety of other methods, including various replaceably coupling techniques whereby said clip magazine 102 can be readily coupled to and decoupled from said main body 20.

FIG. 6 is a side sectional view of the forward portion of clip applying device 2, with guide spring means 100 removed. Here, it can be seen that a plurality of hemostatic clips 37 are disposed within the housing 114 of clip magazine 102. The forward portion of each clip 37 is abutted against the bail portion of the next succeeding clip 37. The clips 37 are maintained in this configuration by the confinement of the inner walls of the clip magazine housing 114 and the surface of ratchet bar 110. Also shown in FIG. 6 is leaf spring 112 which is adapted to conform to the bail portion of clips 37 so that it can prevent the rearward movement of clip 37' when clip feed blade 18 moves in a rearward direction. It can also be seen in FIG. 6 that upper jaw portion 32 has a groove 40 and lower jaw portion 34 has a groove 42, each adapted to allow a clip 37 to slide therethrough. To aid in the forward movement of clips 37 through grooves 40 and 42, upper jaw portion 32 and lower jaw portion 34 have ramp portions 116 configured to guide each clip 37 into grooves 40 and 42.

In FIGS. 7 and 8, top and side views of guide spring means 100 are illustrated respectively. Guide spring means 100 has tab portions 101 configured to allow their coupling to main body 20. Guide spring means 100 also has a forward portion 99 which is bent inward so as to hold clips 37 such that they may be fed forward by clip feed blade 18. FIGS. 9 through 14 illustrate the progressive movement of clips 37 within clip magazine 102 and jaw portions 32 and 34. FIG. 9 is a top cross-sectional view of a portion of clip applying device 2 shown with upper finger loop 5 and feed blade pivot 17 in its extreme retracted position. In this position clip feed blade 18 lies just behind clip 37' which clip is ready to be moved forward from key position 125 through jaw portions 32 and 34. It can be seen in FIG. 9 that ratchet blade 110 is coupled to clip feed blade 18 by means of ratchet blade pin 109 which extends into slot 84 of feed blade 18. Because finger loop 5 is in its extreme retracted position, ratchet blade pin 109 is abutting the extreme left end of slot 84. Also disposed within clip housing 114 is pawl 118 with its tab 120 disposed in one of many ratchet blade holes 111. Pawl 118 is positioned so as to abut the rearward most clip 37.

FIG. 10 is a side cross-sectional view of a portion of clip applying device 2 with finger loop 5 also in its extreme retracted position. In this FIGURE it can be seen that clip feed blade 18 has a lost motion slot 84 wherein is disposed ratchet blade pin 109. Pawl 118 is shown in its extreme rearward position having tab 120 located in one ratchet blade hole 111, and arm portions 122. The leading edge 124 of pawl 118 is configured so as to conform to the bail portion of clips 37. As will be described more fully hereinbelow, pawl 118 is adapted to move clips 37 foward through magazine 102 when ratchet blade 110 is moved forward. FIG. 10 also illustrates leaf spring 112 which is adapted to prevent the rearward movement of clip 37'.

FIG. 11 is a cross-sectional top view of a portion of clip applying device 2 when finger loop 5 has been moved forward. It can be seen in FIG. 11 that finger loop 5 has been moved forward such that ratchet blade pin 109 has traversed the length of lost motion slot 84 of feed blade 18. Because ratchet blade pin 109 is configured so as to slide in slot 84, this forward motion of clip feed blade 18 has not produced forward movement of ratchet blade 110. Correspondingly, the lack of forward movement of ratchet blade 110 has resulted in the lack of forward movement of pawl 118 and the lack of forward movement of clips 37.

FIG. 12 is a side cross-sectional view of a portion of clip applying device 2 illustrating the same amount of forward movement of finger loop 5 as is illustrated in FIG. 11. Ratchet blade pin 109 has thus traversed the length of lost motion slot 84 of clip feed blade 18. Because the forward movement of clip feed blade 18 has not resulted in forward movement of ratchet blade 110, clips 37 have remained stationary, while clip 37' has been moved forward by clip feed blade 18. It can be seen in FIG. 12 that clip feed blade 18 has a forward portion 24 adapted to conform to the bail portion of clips 37. In the presently preferred embodiment, portion 24 is generally of a "V" configuration.

FIG. 13 is a cross-sectional top view of a portion of clip applying device 2 wherein finger loop 5 has been moved to its full forward position. Because previous forward movement of finger loop 5 had brought about abutment of ratchet blade pin 109 with the end of lost motion slot 84, the further forward movement of finger loop 5 has resulted in movement of ratchet blade 109 and thus, forward movement of pawl 118. The forward movement of pawl 118 has, in turn, caused forward movement of clips 37 disposed within magazine 102. In addition, the full forward movement of finger loop 5 has caused clip feed blade 18 to travel through much of upper jaw portion 32 and lower jaw portion 34 and thereby place clip 37' at the extreme end of jaw portions 32 and 34. Thus, this full forward movement of finger loop 5 has placed a clip in the loaded position in jaw portions 32 and 34 so that it is now ready to be placed about a blood vessel or the like.

FIG. 14 is a cross-sectional side view of clip magazine 102 where, just as in FIG. 13, finger loop 5 has been brought to its full forward postion such that further forward movement is prevented. Here, it can be seen that ratchet blade pin 109, which is abutting the right most portion of lost motion slot 84, has now been moved forward by the forward movement of clip feed blade 18. The forward movement of ratchet blade pin 109 has caused ratchet blade 110 to also move forward. Because tab 120 of pawl 118 is disposed in one of the plurality of holes 111 of ratchet blade 110, the forward movement of ratchet blade 110 has resulted in the forward movement of pawl 118. Then, this forward movement of pawl 118 has caused a series of clips 37 contained in magazine 102 to also move forward. Furthermore, this continued forward movement of finger loop 5 has caused clip feed blade 18 to guide a clip 37' through jaw portions 32 and 34 to the extreme portions thereof.

FIG. 19 further illustrates the consequence of the full forward movement of finger loop 5. The forward movement of pawl 118 and clips 37 has now placed a new clip in key position 125. The new clip 37 is held in key position 125 by guide spring means 100. Thus, the full forward movement of finger loop 5 has not only placed clip 37' in the extreme end of jaw portions 32 and 34, but has also resulted in the placement of a new clip 37 in the key position 125 so that it may be ready for later placement in jaw portions 32 and 34. It can also be seen in FIG. 19 that retraction of finger loop 5 and the corresponding retraction of feed blade 18 will allow clip 37 in key position 125 to drop onto housing 114 when feed blade 18 has exited key position 125. This rearward movement of feed blade 18 does not result in rearward movement of the clip 37 located in key position 125 because leaf spring 112 abuts the bail portion of clip 37 and thereby retains clip 37 in the key position 125. In addition, rearward movement of clip feed blade 18 does not create rearward movement of the other clips 37 because pawl 118 has extending arm portions 122 which frictionally engage the inner walls of housing 114. Thus, when clip feed blade 18 moves rearward, pawl 118 remains stationary while its tab portion 120 moves outward so that ratchet blade 110 slides over pawl 118. When clip feed blade 18 has returned to its rear-most position, tab portion 120 of pawl 118 will again drop in a hole 111 of ratchet blade 110, but the hole 111 will be adjacent the hole where tab 120 previously was disposed. In this manner, sequential forward and rear-ward movement of ratchet blade 110 causes pawl 118 to progressively move forward, from one hole 111 to the next hole 111. Such progressive movement of pawl 118 causes, in turn, the progressive forward movement of clips 37.

In FIGS. 15a, b, c and d, are illustrated the operation of safety ratchet 104. In FIG. 15a, upper finger loop 5 is in its extreme retracted position so that ratchet 104 with its teeth 108 are not in contact with ratchet spring 106. Thus, initial forward movement of finger loop 5 is unrestricted by ratchet 104. In FIG. 15b, finger loop 5 has been moved forward such that teeth 108 of ratchet 104 are abutting ratchet spring 106. In FIG. 15c, the upper finger loop 5 has been moved farther forward so that ratchet spring 106 is now disposed in teeth 108 of ratchet 104. It can be seen from FIG. 15c that rearward movement of finger loop 5 is prevented by the flexing of spring 106 due to the engagement of spring 106 and teeth 108. Continued forward movement of finger loop 5 is allowed as ratchet spring 106 glides over teeth 108 of ratchet 104 until spring 106 is disposed in well 107. At this point, feed blade 18 has moved clip 37 to the fully loaded position so that feed blade 18 can again be returned to its fully retracted position while ratchet spring 106 glides over teeth 108 of ratchet 104.

FIG. 16.is a cross-sectional end view of clip applicating device 2 taken along line 16—16 of FIG. 6. Here it can be seen that upper jaw pivot 36 extends through lower finger loop member 7 which is adjacent main body 20. Coupled to the exterior of main body 20 is guide spring means 100 with its tab portions 101 coupled to main body 20. Disposed under guide spring means 100 is main housing 114, containing clips 37 and clip 37' in the key position 125.

FIG. 17 is a cross-sectional end view of clip applicating device 2 taken through the lines 17—17 of FIG. 6. Again, upper jaw pivot 36 is shown extending through lower finger loop member 7 which is adjacent main body 20. Coupled to the outer exterior of main body 20 is clip magazine housing 114 wherein is disposed clip feed blade 18, ratchet blade 110, and clip 37. FIG. 18 is a cross sectional view of clip applying device 2 taken along lines 18—18 of FIG. 10. Coupled to the exterior of main body 20 is guide spring means 100 with its tab portions 101. Disposed within guide spring means 100 is clip magazine housing 114 wherein is disposed pawl 118, ratchet blade 110, feed blade 18, and ratchet blade pin 109.

It can be seen from the above description and particularly FIGS. 1 and 5 that clip applicating device 2 of the present invention provides an automatic feeding and crimping of hemostatic clips 37. By simplying moving upper and lower finger loops 4 and 6 outwardly and then inwardly, a clip is moved from an external magazine 102, and disposed in jaw portions 32 and 34 where it is deformed around a blood vessel or the like. This process of inward and outward movement of finger loops 4 and 6 may be repeated rapidly, so that one vessel after another is closed by hemostatic clips 37, until the supply of clips in magazine 102 is depleted.

The clip applicating device 2 of the present invention provides the further advantage of high visability to the user. Because the device 2 is of an extremely thin design, essentially the width of currently used hemostats and because jaw portions 32 and 34 are curved away from the main body 20, a surgeon using clip applying device 2 will have a clear view of the vessel he is closing and, in addition, will be able to reach remote and obscure regions for further vessel closure. In addition, clip applying device 2 is constructed so as to prevent a clip 37 from accidentally dropping from the device, thereby obviating a great deal of inconvenicence and lost time. Furthermore, due to the extensive use of stamped parts, as opposed to machined parts, and due to the few number of moving parts, the clip applicating device 2 can be manufactured and sold relatively inexpensively. This inexpensive cost, in turn, allows the device to be pre-sterilized by the manufacturer so that it can be used once and then discarded.

There has been described herein a new and novel clip applying device which has special utility for applying hemostatic clips to blood vessels and the like. However, it is to be understood that various alternate embodiments using the principles of the present invention may be readily incorporated. Thus, while specific embodiments of the present invention have been disclosed and described in detail herein, it will be understood by those skilled in the art that various changes in form and detail may be made therein without departing from the spirit and scope of the invention.

We claim:

1. A clip magazine adapted to be externally attached to a surgical clip applying device having clip deforming means for receiving and deforming clips, comprising:
   (i) a housing wherein a plurality of clips are stored; and
   (ii) a laminated clip feed means slideably disposed within said housing and adapted to slide into and out of said clip deforming means, for sequentially moving said clips to said clip deforming means, said laminated clip feed means comprising a plurality of thin blades which are uncoupled from each other over a portion of their length.

2. The clip magazine of claim 1 wherein said clip feed means is an elongated member longitudinally disposed within said housing.

3. The clip magazine of claim 2 wherein said clip feed means includes a leading edge adapted to generally conform to the bail portion of said clips.

4. The clip magazine of claim 3 wherein said leading edge of said clip feed means is generally "V" shaped.

5. The clip magazine of claim 2 wherein said clip feed means is a blade member comprised of a plurality of laminated strips adapted to move longitudinally while bending laterally.

6. The clip magazine of claim 5 wherein said feed means includes a generally "V" shaped leading edge.

7. A clip magazine adapted to be externally attached to a surgical clip applying device having clip deforming means for receiving and deforming clips, comprising:
   (i) a housing wherein a plurality of clips are stored;
   (ii) a laminated clip feed means slideably disposed within said housing and adapted to slide into and out of said clip deforming means, for sequentially moving said clips to said clip deforming means; and
   (iii) a clip loading means slideably disposed within said housing and selectively coupled to said clip feed means.

8. The clip magazine of claim 7 wherein said clip loading means comprises a ratchet bar selectively coupled to said clip feed means and a pawl means selectively coupled to said ratchet bar for urging said clips through said housing.

9. The clip magazine of claim 8 wherein said ratchet bar has a plurality of apertures disposed therethrough and said pawl means has a resilient tab portion adapted to selectively engage said apertures such that forward movement of said ratchet bar causes forward movement of said pawl means.

10. The clip magazine of claim 9 wherein said pawl means has arm portions adapted to frictionally engage said housing for preventing rearward movement of said pawl means.

11. The clip magazine of claim 10 wherein said clip feed means has an elongated aperture disposed therethrough and said ratchet bar has a pin member coupled thereto and adapted to slide through said feed means aperture such that initial forward movement of said feed means does not result in forward movement of said ratchet bar while additional forward movement of said feed means results in forward movement of said ratchet bar.

12. The clip magazine of claim 11 wherein said pawl means has a leading edge adapted to correspond to the bail portion of said clip.

13. The clip magazine of claim 12 wherein said pawl means has a generally "V" shaped leading edge.

14. The clip magazine of claim 13 wherein said housing further includes a guide spring coupled thereto.

15. A clip magazine adapted to externally couple to a surgical clip applying device comprising:
   (i) a housing wherein a plurality of clips are stored;
   (ii) clip feed means slideably disposed within said housing for sequentially ejecting said clips therefrom, and
   (iii) a clip loading means, slideably disposed within said housing and selectively coupled to said clip feed means, for loading clips in the clip feed means, said clip loading means including a ratchet bar selectively coupled to said clip feed means and a pawl means selectively coupled to said ratchet bar, for urging said clips through said housing, and said ratchet bar having a plurality of apertures disposed therethrough and said pawl means having a resilient tab portion adapted to selectively engage said apertures such that forward movement of said ratchet bar causes forward movement of said pawl means.

16. The clip magazine of claim 15 wherein said pawl means has arm portions adapted to frictionally engage said housing for preventing rearward movement of said pawl means.

17. The clip magazine of claim 16 wherein said clip feed means has an elongated aperture disposed therethrough and said ratchet bar has a pin member coupled thereto and adapted to slide through said feed means aperture such that initial forward movement of said feed means does not result in forward movement of said ratchet bar while additional forward movement of said feed means results in forward movement of said ratchet bar.

18. The clip magazine of claim 15 wherein said pawl means has a leading edge adapted to correspond to the bail portion of said clip.

19. The clip magazine of claim 18 wherein said pawl means has a generally "V" shaped leading edge to engage the trailing clip.

20. The clip magazine of claim 19 wherein said housing further includes a guide spring coupled thereto for guiding a clip from the clip loading means to the clip feed means.

21. A clip magazine for a surgical clip applicator device having jaw means for deforming a clip and a first member for actuating the clip magazine, comprising:
   a housing defining a groove for slidably holding a series of clips arranged in a longitudinal line with respect to the applicator; and
   clip loading means having a second member, for advancing the series of clips along the groove when the first member is actuated, to sequentially place each clip in a predetermined position to be fed to the jaw means; said clip loading means further having a slot in one of said first and second members and a pin carried by the other of said first and second members, said pin being disposed within the slot wherein an initial movement of the first member does not result in substantial movement of the second member until the pin engages an end of the slot wherein further movement of the first member actuates the second member of the clip loading means, and a subsequent reverse movement of the first member does not result in substantial movement of the second member until the pin engages the other end of the slot wherein further reverse movement of the first member retracts the second member of the clip loading means 22. The magazine of claim 21 wherein the first member comprises a clip feed bar for moving clips from the magazine to the jaw means and the second member comprises a ratchet bar.

23. A clip magazine adapted to be attached to a surgical clip applying device, comprising:
  a housing defining a groove for slideably holding a plurality of clips arranged in a longitudinal line with respect to the magazine;
  a ratchet bar positioned parallel to said groove, and a pawl means selectively coupled to said ratchet bar for engaging the clips within the groove and for urging said clips through said groove,
  wherein a movement of the ratchet bar in a first direction causes the pawl means to couple to the ratchet bar and move with the ratchet bar and a reverse movement of the ratchet bar uncouples the pawl means from the ratchet bar.

24. A clip magazine adapted to be attached to a surgical clip applying device having clip deforming means for receiving and deforming clips, and clip feed means for sequentially moving said clips to said clip deforming means, said magazine comprising:
  (i) a housing wherein a plurality of clips are stored; and
  (ii) a clip loading means slideably disposed within said housing and selectively coupled to said clip feed means, for loading clips in the clip feed means.

25. The clip magazine of claim 24 wherein said clip loading means comprises a ratchet bar selectively coupled to said clip feed means and a pawl means selectively coupled to said ratchet bar for urging said clips through said housing.

26. The clip magazine of claim 25 wherein said clip feed means has an elongated aperture disposed therethrough and said ratchet bar has a pin member coupled thereto and adapted to slide through said feed means aperture such that initial forward movement of said feed means does not result in forward movement of said ratchet bar while additional forward movement of said feed means results in forward movement of said ratchet bar.

27. The clip magazine of claim 25 wherein said ratchet bar has a plurality of apertures disposed therethrough and said pawl means has a resilient tab portion adapted to selectively engage said apertures such that forward movement of said ratchet bar causes forward movement of said pawl means.

28. The clip magazine of claim 27 wherein said pawl means has arm portions adapted to frictionally engage said housing for preventing rearward movement of said pawl means.

29. The clip magazine of claim 27 wherein said pawl means has a leading edge adapted to correspond to the bail portion of said clip.

30. The clip magazine of claim 27 wherein said pawl means has a generally "V" shaped leading edge.

31. The clip magazine of claim 24 wherein said housing further includes a guide spring coupled thereto.

32. A clip magazine for a surgical clip applicator device having jaw means for deforming a clip, and a clip feed blade for moving clips from the magazine to the jaw means, said magazine comprising:
  a housing for holding a plurality of clips;
  clip loading means having a member for advancing the clips through the magazine when the member is actuated in a reciprocating motion; and
  lost motion means for coupling the feed blade to the loading means member wherein a reciprocating motion of the clip feed blade causes a shorter reciprocating motion of the loading means member.

* * * * *